United States Patent [19]

Mase et al.

[11] Patent Number: 4,861,456

[45] Date of Patent: * Aug. 29, 1989

[54] ELECTROCHEMICAL DEVICE

[75] Inventors: Syunzo Mase, Aichi; Shigeo Soejima, Nagoya, both of Japan

[73] Assignee: NGK Insulators, Ltd., Nagoya, Japan

[*] Notice: The portion of the term of this patent subsequent to Apr. 1, 2003 has been disclaimed.

[21] Appl. No.: 119,281

[22] Filed: Nov. 9, 1987

Related U.S. Application Data

[63] Continuation of Ser. No. 858,826, Apr. 29, 1986, abandoned, which is a continuation of Ser. No. 670,878, Nov. 13, 1984, abandoned.

[30] Foreign Application Priority Data

Nov. 18, 1983 [JP] Japan .................................. 58-218399

[51] Int. Cl.$^4$ ............................................ G01N 27/58
[52] U.S. Cl. ..................................... 204/425; 204/412;
204/424; 204/426; 204/428; 204/429
[58] Field of Search ............... 204/412, 424, 425, 426, 204/427, 428, 429

[56] References Cited

U.S. PATENT DOCUMENTS

| | | | |
|---|---|---|---|
| 4,158,166 | 6/1979 | Isenberg | 204/426 X |
| 4,224,113 | 9/1980 | Kimura et al. | 204/425 X |
| 4,272,329 | 6/1981 | Hetrick et al. | 204/412 X |
| 4,282,080 | 8/1981 | Muller et al. | 204/412 |
| 4,298,573 | 11/1981 | Fujishiro | 204/426 X |
| 4,300,990 | 11/1981 | Maurer | 204/412 |
| 4,334,974 | 6/1982 | Muller et al. | 204/426 |
| 4,416,763 | 11/1983 | Fujishiro | 204/429 X |
| 4,428,817 | 1/1984 | Isenberg | 204/427 X |
| 4,450,065 | 5/1984 | Yamada et al. | 204/412 |
| 4,505,806 | 3/1985 | Yamada | 204/427 X |
| 4,505,807 | 3/1985 | Yamada | 204/428 X |
| 4,579,643 | 4/1986 | Mase et al. | 204/429 X |

Primary Examiner—Nam X. Nguyen
Attorney, Agent, or Firm—Arnold, White & Durkee

[57] ABSTRACT

An electrochemical device such as an oxygen sensor comprising a plurality of solid electrolyte bodies, at least one pair of electrodes, each pair being disposed such that the electrodes are held in contact with the solid electrolyte bodies separately, at least one conductor sandwiched by two adjacent ones of the solid electrolyte bodies, and at least one electrical insulation layer. A substantive portion of at least one side of the conductor indirectly contacts with one of the two adjacent solid electrolyte bodies via the electrical insulation layer which is disposed therebetween, whereby the conductor is protected from direct contact with the associated solid electrolyte body. The insulation layer further serves to prevent noises which could otherwise be produced due to leakage current from the conductor. The conductor may be a lead connected to one of the electrodes, or a heater for heating a portion of the solid electrolyte body adjacent to the electrodes.

15 Claims, 5 Drawing Sheets

ELECTROCHEMICAL DEVICE

This is a continuation of application Ser. No. 858,826, abandoned filed Apr. 29, 1986 which in turn is a continuation application of 670,878, filed Nov. 13, 1984, abandoned.

BACKGROUND OF THE INVENTION

The present invention relates generally to an electrochemical device, and more particularly to a device which comprises a laminated electrochemical cell having planar solid electrolyte bodies.

There have been known various electrochemical devices using solid electrolyte, for example as oxygen sensors to detect the oxygen concentration of an exhaust gas from internal combustion engines of automotive vehicles. The typical examples of such oxygen sensors include: an oxygen sensor which comprises a tubular body of oxygen-ion conductive solid electrolyte such as zirconia ceramics, and electrodes of platinum or the like provided on both inner and outer surfaces of the tubular solid electrolyte body, and which operates to determine the oxygen concentration according to the principle of an oxygen concentration cell; an oxygen sensor similar to the above, which incorporates a heater which enables the sensor to operate at a relatively low exhaust gas temperature; and a so-called "lean-burn" sensor suitable for detecting the oxygen concentration of an exhaust gas which is produced at lean air-fuel ratios, i.e., an exhaust gas having a larger oxygen content. Also known in the art are electrochemical devices such as sensing and pumping elements for detecting hydrogen, nitrogen, carbon dioxide gas, etc. These sensing and pumping elements operate according to the principle of a concentration cell, like the oxygen sensor indicated above.

In such electrochemical devices, solid electrolyte materials have been generally used in the form of a tubular body which has an elongate bore closed at its one end. In recent years, however, it has been attempted to replace the tubular solid electrolyte body with a solid electrolyte body of planar shape, as disclosed in U.S. Pat. No. 4,334,974, in view of relatively low productivity and high cost of manufacture of the solid electrolyte bodies of tubular shape, and from the standpoint of easy assembling of parts with the solid electrolyte body. When such planar solid electrolyte bodies are employed, suitable electrodes are disposed in contact with the surfaces of the planar body of solid electrolyte, and the electrolyte bodies and other parts are assembled into a laminar structure constituting an electrochemical cell.

In such an electrochemical cell wherein planar or plate-like bodies of solid electrolyte are laminated, each of conductors such as a heating element of a heater and leads for the electrodes and the heating element is sandwiched between a pair of adjacent planar solid electrolyte bodies, that is, the conductors are embedded in the mass of the solid electrolyte. Accordingly, the conductors are held in direct contact with the solid electrolyte. Since the electrochemical device is adapted such that a voltage is applied, for example, to an oxygen pumping element through such conductors (conductive leads), parts of the solid electrolyte contacting the conductors are electrolyzed and tend to be deteriorated. Thus, the solid electrolyte bodies have potential problems of cracking, and deterioration or loss of the ion conductivity and other characteristics. Further, the electrolysis of the solid electrolyte may cause an erroneous measurement between the conductor and a measuring electrode, which affects an electromotive force to be measured, and causes a measurement error of the electrochemical device. In addition, an air gap exists between the conductor and the solid electrolyte bodies sandwiching the conductor. This air gap accommodates an oxygen gas, which may cause degradation of the response and generation of output noises of the sensing device. In the case where a heater is embedded in the solid electrolyte for heating exhaust or other gases to be measured when their temperature is low, the heater tends to serve as a conductor and therefore may cause problems as indicated above.

SUMMARY OF THE INVENTION

It is accordingly an object of the present invention, which was made in the light of the above situations in the prior art, to provide an electrochemical device which is effectively protected against electrolysis of parts of the solid electrolyte adjacent to the conductors embedded in the solid electrolyte.

Another object of the invention is the provision of a highly reliable electrochemical device of laminar or integrally laminated type, which suffers minimum noises and measurement errors caused by the conductors embedded in the solid electrolyte, and which is thus improved in response.

According to the present invention, there is provided an electrochemical device comprising: a plurality of solid electrolyte bodies; at least one pair of electrodes; at least one conductor; and at least one electrical insulation layer. Each pair of the electrodes is disposed such that the electrodes are held in contact with the solid electrolyte bodies separately. The conductor is sandwiched by two adjacent ones of the solid electrolyte bodies, and each of the at least one electrical insulation layer is disposed between one side of the conductor and one of said two adjacent solid electrolyte bodies. The insulation layer covers at least a substantive portion of the conductor.

In the electrochemical device constructed as described above, an electrical insulation layer or layers electrically insulate an electric conductor or conductors, such as a lead connected to one of the electrodes, a heating element and/or leads connected to the heating elements, which are disposed between two adjacent solid electrolyte bodies. With the provision of the insulation layers, the solid electrolyte bodies are substantially completely protected against electrolysis which would otherwise occur due to application of a voltage to the conductors. Thus, the insulation layers are effective to prevent cracking, deterioration or other troubles with the solid electrolyte bodies arising from the electrolysis. Further, the insulation layers serve as effective means for preventing output noises of the electrochemical device which would otherwise be produced due to the uninsulated conductors. Accordingly, the electrochemical device of the invention is highly reliable in operation, and suitably usable as various sensors for determining or controlling the concentration of specific components of a fluid associated with electrode reaction, such as nitrogen, carbon dioxide and hydrogen as well as oxygen, in particular as an oxygen sensor for determining the oxygen concentration of an exhaust gas emitted from an internal combustion engine. The present invention finds its primary industrial significance in such fields of technology.

According to a preferred form of the invention, the conductor or conductors are made of a material including elements of the platinum group, and the electrical insulation layer is made of a material consisting essentially of alumina or spinel.

In accordance with one advantageous embodiment of the invention, a substantial portion of the conductor is sandwiched on opposite sides thereof by two electrical insulation layers one of which is disposed between said one side of the conductor and said one of the two adjacent solid electrolyte bodies, and the other of which is disposed between the other side of the conductor and the other of said two adjacent solid electrolyte bodies.

When the conductor is a lead connected to one of said pair of electrodes, and said two adjacent solid electrolyte bodies includes said one of the solid electrolyte bodies, the other of the electrodes is a measuring electrode which is exposed to the gaseous fluid, while said one of the electrodes is a reference electrode which is exposed to a reference gas. The measuring and reference electrodes generate an electromotive force which varies with a difference in concentration of the measuring component between the gaseous fluid and the reference gas.

According to one form of the above embodiment wherein the conductor is a lead of one of the electrodes, the other of said two adjacent solid electrolyte bodies has a cavity into which the reference gas is introduced, so that said one of the electrodes is exposed to the reference gas within the cavity.

According to another advantageous embodiment of the invention, there is provided an electrochemical device for determining the concentration of a component of a gaseous fluid, comprising:

a pumping cell of laminar structure including a first planar solid electrolyte body, a pair of pumping electrodes disposed in contact with opposite sides of said first planar solid electrolyte bodies, and a pair of first leads connected at each one end thereof to each one of said pumping electrodes and at the other ends to an external power source;

a planar spacer member made of a solid electrolyte material cooperating with said first planar solid electrolyte body to sandwich one of said first leads;

a sensing cell of laminar structure including a second planar solid electrolyte body, a pair of measuring electrodes disposed in contact with opposite sides of said second planar solid electrolyte body, and a pair of second lead connected at each one end thereof to each one of said measuring electrodes and at the other ends to an external measuring device, the laminar structures of said pumping cell and sensing cell being disposed so as to sandwich said spacer member;

a first and a second electrical insulation layer disposed between one side of said one of the first leads and said first planar solid electrolyte body, and between the other side of said one of the first leads and said spacer member, respectively; and a third electrical insulation layer disposed between one of said second leads and said second planar solid electrolyte body.

In accordance with a preferred form of the above embodiment, the spacer member has a cavity to and from which the component of said gaseous fluid is introduced and removed upon application of a voltage between said pumping electrodes. The pumping electrode connected to the first lead, and the measuring electrode connected to the second lead, may both be exposed to an atmosphere within said cavity formed in the spacer member.

BRIEF DESCRIPTION OF THE DRAWING

The foregoing and other objects, features and advantages of the present invention will become more apparent from reading the following description of preferred embodiments taken in connection with the accompanying drawing in which.

DETAILED DESCRIPTION OF THE PREFERRED EMBODIMENTS

Referring to the accompanying drawings illustrating preferred embodiments of the present invention, the arrangement of the invention will be described in detail.

Figure 1:
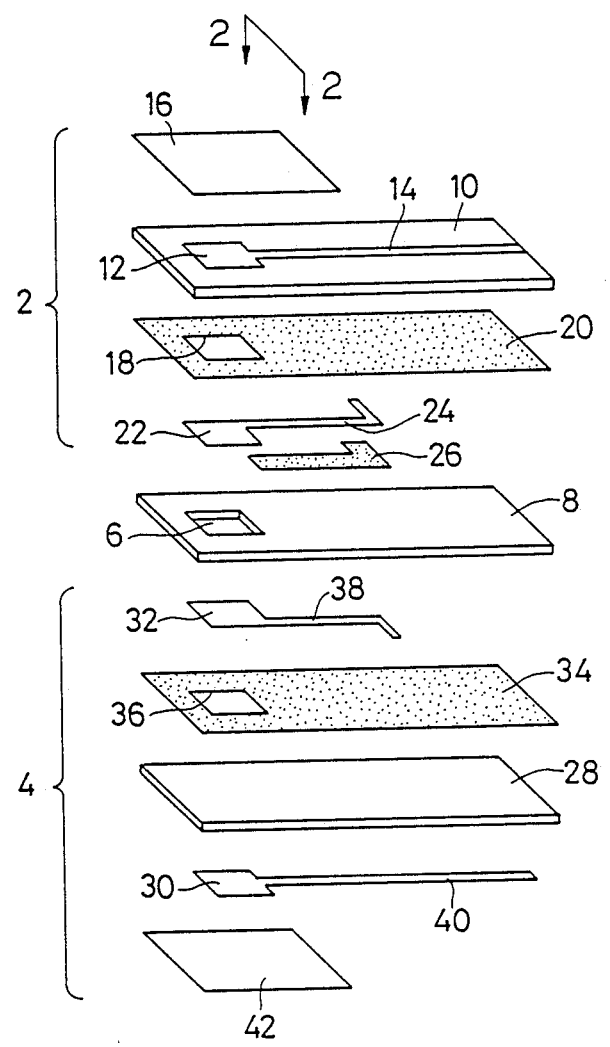
FIG. 1 is an exploded perspective view of a sensing element of one embodiment of an electrochemical device of the invention in the form of an oxygen sensor.

There is shown in the exploded perspective view of FIG. 1 a sensing element of one example of an oxygen concentration sensor which is one embodiment of an electrochemical device of the invention. The oxygen concentration sensor comprises a lean-burn sensor which is an integral lamination of a pumping cell 2 of laminar structure and a sensing cell 4 also of laminar structure via a planar spacer member 8 sandwiched therebetween. The spacer member 8 is made of a solid electrolyte material such as zirconia ceramics and has a cavity 6.

The pumping cell 2 includes a solid electrolyte body 10 of plate-like or planar shape made of zirconia ceramics or the like, and a porous outer pumping electrode 12 made of platinum, for example, which is disposed on one of opposite sides or surfaces of the planar solid electrolyte body 10. More specifically, the planar solid electrolyte body 10 is provided with the outer pumping electrode 12 on its surface on the side which is exposed to an exhaust gas or other gases to be measured. The outer pumping electrode 12 is connected to an external power source through a conductor in the form of a lead 14 extending from the electrode 12. The outer pumping electrode 12 is covered with a porous protective layer 16 formed of porous spinel or the like by means of plasma spray technique, screen printing or the like and exposed to the measurement gas through the protective layer 16.

The pumping cell 2 further includes an electrical insulation layer 20 which is disposed on the other side of the planar solid electrolye body 10. The insulation layer 20 has a cutout 18 of a size corresponding to the size of the outer pumping electrode 12. An inner pumping electrode 22 is disposed on the side of the insulation layer 20 remote from the solid electrolyte body 10 such that the electrode 22 is aligned with the cutout 18 formed in the insulation layer 20. The inner pumping electrode 22 is provided with a lead 24 of a conductive material which extends over the insulation layer 20 so that its end is located outside the pumping cell 2. Another electric insulation layer 26 is disposed on the side of the lead 24 remote from the insulation layer 20, whereby the lead 24 is sandwiched on its opposite sides by the two electrical insulation layers 20 and 26. In other words, the lead 24 is covered by the insulation layers 20, 26 at its upper and lower surfaces except the outer end portion which is exposed outside the pumping cell 2 for electric connection to the external power source.

As described above, the pumping cell 2 comprises an oxygen pumping cell which includes a pair of pumping electrodes, i.e., the outer pumping electrode 12 formed on one side of the solid electrolyte body 10, and the inner pumping electrode 22 disposed adjacent to the cutout 18 in the insulation layer 20 on the other side of the solid electrolyte body 10. With a voltage applied between these two electrodes 12 and 22, the oxygen pumping cell operates in the well known manner, to introduce the oxygen in the outside measurement gas into the cavity 6 formed in the spacer member 8, or to discharge or remove the oxygen from the cavity 6 out into the outside measurement gas, according to the direction of flow of an electric current between the electrodes 12 and 22.

In the meantime, the sensing cell 4 includes a planar solid electrolyte body 28 made of zirconia ceramics or the like, and further includes an inner measuring electrode 32 and an outer measuring electrode 30 which adhere to opposite surfaces of the planar solid electrolyte body 28. Thus, an oxygen concentration cell is constituted. Between the two inner and outer measuring electrodes 32, 30, there is interposed an electrical insulation layer 34 which has a cutout 36 aligned with the inner measuring electrode 32, so that the inner electrode 32 is disposed on the solid electrolyte body 28 via the cutout 36. The inner measuring electrode 32 is connected to a lead 38 which is electrically insulated by the insulation layer 34 with respect to the planar solid electrolyte body 28. The lead 38 extends out of the sensing cell 4 so that its end opposite to the electrode 30 is connected to a suitable measuring device. The outer measuring electrode 30 is connected via its lead 40 to the external measuring device, and covered at its outer surface with a porous protective layer 42 similar to the aforementioned porous protective layer 16. That is, the protective layer 42 protects the outer measuring electrode 30 from direct contact of the measurement gas. In the above-described arrangement of the sensing cell 4, an electromotive force due to difference in oxygen concentration is measured between the outer measuring electrode 30 which is exposed to the outside measurement gas, and the inner measuring electrode 32 which is exposed to the atmosphere within the cavity 6.

The laminar pumping cell 2 and the laminar sensing cell 4, and the spacer member 8 are laminated with the spacer member 8 sandwiched between the two cells 2, 4, whereby the intended laminar electrochemical cell (sensing element) is fabricated. In this arrangement, the conductors interposed between the two masses of solid electrolyte, i.e., the leads 24 and 38 of the electrodes 22 and 32 are electrically insulated substantially along their entire length, that is, at the portions which are exposed to an elevated temperature, with respect to at least one of the two masses of solid electrolyte. Stated more particularly with reference to FIG. 2, the lead 24 of the inner pumping electrode 22 is sandwiched by the electric insulation layers 20 and 26, and thus electrically insulated with respect to the planar solid electrolyte body 10 and the spacer member 8 (made of solid electrolyte) which are disposed on both sides of the lead 24. On the other hand, the lead 38 of the inner measuring electrode 32 is electrically insulated by the insulation layer 34 with respect to the planar solid electrolyte body 28 on one side of the lead 38.

In the electrochemical device of the aforementioned construction wherein the lead 24 of the inner pumping electrode 22 sandwiched by the insulation layers 20, 26 is not in direct contact with the solid electrolyte members 10, 8, the portions of the solid electrolyte members which would otherwise contact the lead 24 will not be deteriorated due to electrolysis upon application of a pumping voltage between the inner and outer pumping electrodes 12, 22 to operate the pumping cell 2 as an oxygen pumping cell. Hence, the spacer member 8 and the planar solid electrolyte body 10 are protected against otherwise possible troubles of cracking, and deterioration of ion conductivity. In this connection, it is noted that the lead 14 of the outer pumping electrode 12, which directly contacts the solid electrolyte body 10, will not be subject to the previously indicated electrolysis at its portion contacting the solid electrolyte body 10, because the oxygen in the outside measurement gas is supplied to the solid electrolyte body 10.

Further, the insulation layer 34 prevents the lead 38 of the inner measuring electrode 32 from directly contacting the planar solid electrolyte body 28. Hence, the insulation layer 34 effectively eliminates otherwise possible troubles: such as measurement errors based on measurements of an electromotive force between the conductor lead and the outer measuring electrode; degradation of the response characteristics of the sensing element due to presence of the oxygen gas staying within an air gap existing between the lead of the inner measuring electrode and the planar solid electrolyte bodies; and generation of output noises of the sensing element.

On the other hand, no insulation layer is disposed between the lead 38 and the spacer member 8 and these two members are kept in direct contact with each other. However, the spacer member 8 is electrically insulated by the insulation layers 20, 26 and 34 with respect to the electrodes 12, 22 and 32 and their leads 14, 24 and 38. Therefore, it is not necessary to interpose an electrical insulation layer between the lead 38 and the spacer member 8.

The insulation layers 20, 26 and 34 for electrical insulation of the conductors, i.e., leads 24 and 38 from the solid electrolyte materials 10, 8, 28, are preferably ceramic layers which comprises alumina or spinel as a major component. However, the insulation layers may be made of ceramics whose major component is borosilicate glass or mullite. It is desired that the insulation layers 20, 26 and 34 are fabricated to have a thickness as small as possible within a range in which they can provide sufficient electric insulating capability. Preferably, the thickness should be less than 100 $\mu$m, and more preferably ess than 50 $\mu$m. Further, it is preferred that the insulation layers 20, 26 and 34 are made porous, for effectively minimizing a stress due to difference in coefficient of thermal expansion between these insulation layers and the solid electrolyte materials 8, 10, 28. In other words, the porous structure of the insulation layers is effective for preventing flake-off of these layers and the solid electrolyte members.

The electrical insulation layers 20 and 34 are formed on the planar solid electrolyte bodies 10 and 28, respectively, by applying a paste of ceramic powder, for example by a screen-printing method, to green sheets of the planar solid electrolyte bodies 10, 28. Subsequently, the electrode 22 and its lead 24, and the electrode 32 and its lead 38, are similarly printed on the printed insulation layers 20 and 34, respectively. The insulation layer 26 is similarly printed on the printed lead 24 on the insulation layer 20. The thus prepared lamination comprising the printed layers 20, 22, 24 and 26 on the green sheet of the electrolyte body 10, and the lamination comprising the printed layers 34, 32 and 38 on the green sheet of the electrolyte body 28, are then laminated with the spacer member 8 sandwiched therebetween, and finally subjected to known co-firing and other processes, whereby the laminated electrochemical cells 2 and 4 are obtained in an integral laminar structure.

During a co-firing process as indicated above, the solid electrolyte materials and electrical insulation materials are concurrently sintered. For this reason, it is desired that the electrodes 12, 22, 30 and 32, and their leads 14, 24, 40 and 38 are co-fired with the solid electrolyte and electrical insulation materials. In this instance, these electrodes and leads which are electric conductors are preferably formed by screen printing, using as major components elements of the platinum group including platinum, palladium, rhodium, iridium, ruthenium and osmium. The printed layers are finally fired to form the intended layers of electrodes and leads concurrently with the solid electrolyte and insulation layers. In this respect, it is preferred to admix fine ceramic particles of zirconia, yttria, alumina, etc. with the materials of the conductors, for preventing flake-off and disconnection of the conductors. In this case, the adhesion of the conductors to the adjacent layers after the firing is improved.

The solid electrolyte materials used according to the invention may be aluminium nitride, $SrCeO_3$, solid solution of bismuth oxide-oxide of rare earth element, $La_{1-x}Ca_xYO_{3-\alpha}$, or the like, in place of the previously indicated zirconia ceramics.

Figure 2:
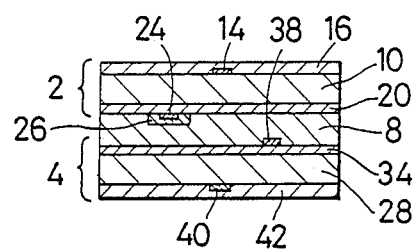
FIG. 2 is an elevational schematic view in cross section taken along line 2—2 of FIG. 1.

The oxygen sensor illustrated in FIGS. 1 and 2 as an electrochemical device of the invention is suitably used as a lean-burn sensor for controlling an engine of the type emitting an exhaust gas of lean air-fuel ratios whose oxygen partial pressure is higher than that of the stoichiometric air-fuel ratio. At a relatively low temperature of the exhaust gas, however, the planar solid electrolyte bodies 10 and 28 may not be held at a sufficiently high temperature. In this condition, the oxygen sensor is not sufficiently capable. For accurate performance at such low exhaust temperature, the oxygen sensor is generally provided with a heater. The principle of the present invention is also applicable to such a heater-equipped sensor, one example of which is illustrated in FIGS. 3 and 4.

Figure 4:
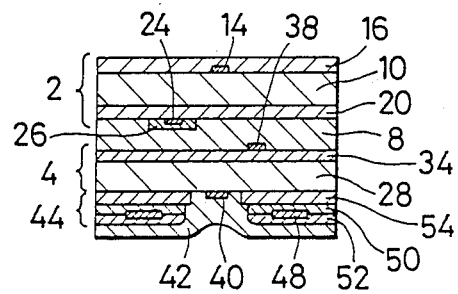
FIGS. 4, 6 and 8 are elevational schematic views in cross section taken along line 4—4 of FIG. 3, line 6—6 of FIG. 5 and line 8—8 of FIG. 7, respectively.
Figure 3:
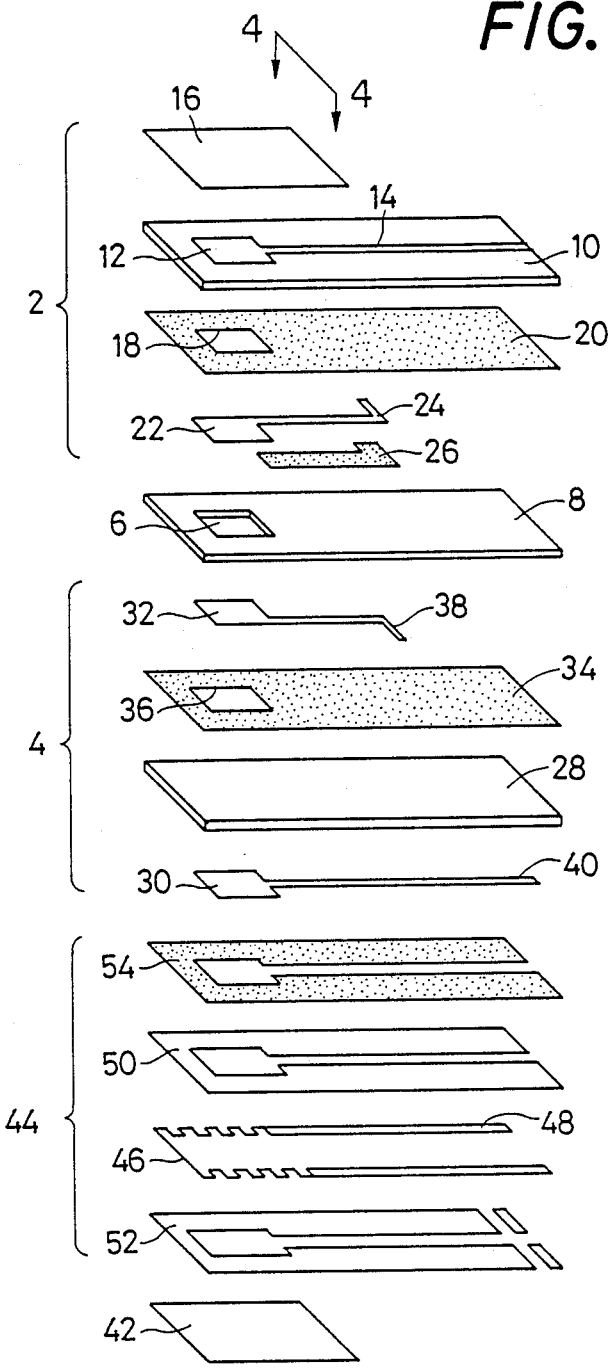
FIGS. 3, 5 and 7 are exploded perspective views corresponding to FIG. 1, of other embodiments of the electrochemical device of the invention, respectively.

The modified oxygen sensor of FIGS. 3 and 4 is different from the sensor of FIGS. 1 and 2 in that a heater 44 is provided on the side of the sensing element 4. Since the arrangements of the pumping and sensing cells 2 and 4 are identical to those of the aforementioned sensor of FIGS. 1 and 2, the same reference numerals are used in FIGS. 3 and 4 to identify the corresponding parts, and the following description of this modified embodiment refers only to the heater 44 for avoiding repeated description of the same parts.

The heater 44 is a lamination of a heating element 46 with leads 48, an inner and an outer gastight ceramic layer 50, 52 disposed on opposite sides of the heating element 46, and an electrical insulation layer 54 which is disposed between the inner gastight ceramic layer 50 and the planar solid electrolyte body 28 and which has the same configuration as the ceramic layer 50. The inner and outer gastight layers 50 and 52 are provided to restrain vaporization of platinum and other components of a composition of the heating element 46 and leads 48. The electrical insulation layer 54 is formed of the same materials as used for the insulation layers 20, 26 and 34 provided in the pumping and sensing elements 2 and 4.

The insulation layer 54 is laminated on the surface of the planar solid electrolyte body 28 on which the outer measuring electrode 30 is disposed. Thus, the insulation layer 54 provides a barrier to protect the sensing cell 4 against otherwise possible leakage of electric current from the heating element 46 and leads 48 through the gastight ceramic layer 50, thereby protecting the sensing cell 4 from an influence of such leakage current.

After the heater 44 has been superposed on the sensing cell 4, a porous protective layer 42 is superposed on the heater 44. The protective layer 42 protects the surface of the outer measuring electrode 30 which is exposed to the measurement gas through a cutout in the insulation layer 54, a cutout in the inner gastight ceramic layer 50, a void defined by the heating element 46, and a cutout in the outer gastight ceramic layer 52. The protective layer 42 also serves to protect an end portion of the lead 40 adjacent to the measuring electrode 30.

As discussed above, the electrochemical device having the heater 44 uses the insulation layers which are similar in construction and location to those used in the device of FIGS. 1 and 2. Accordingly, these insulation layers attain the same functions as previously described.

Figure 5:
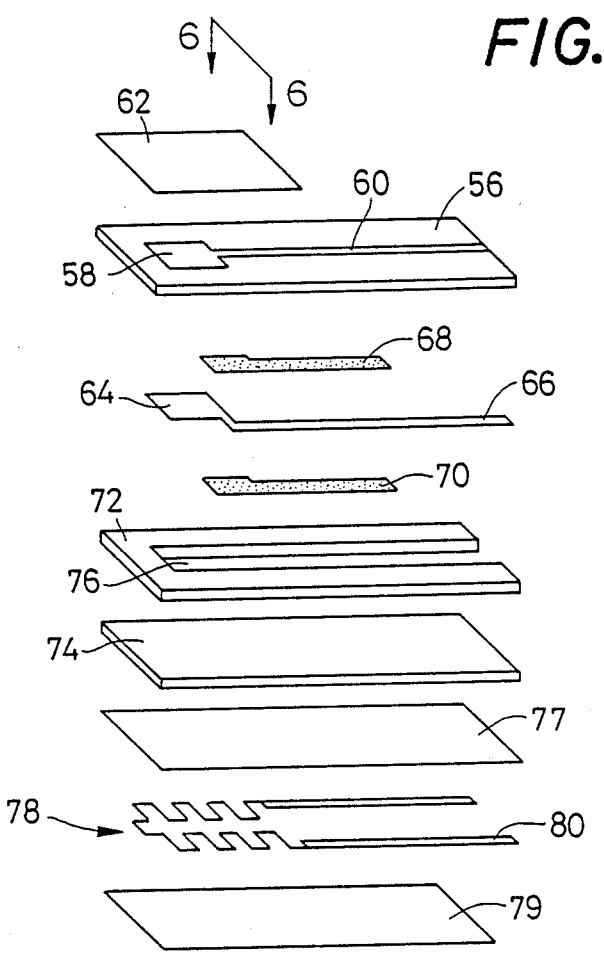
Figure 6:
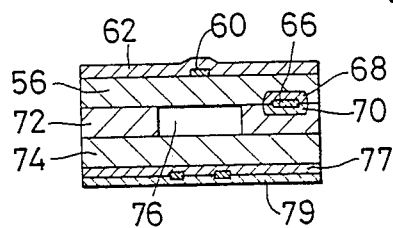

Another modified oxygen sensor as an electrochemical device of the invention is illustrated in FIGS. 5 and 6.

The oxygen sensor of FIGS. 5 and 6, which is a modified embodiment of the electrochemical device of the invention, is a sensor to measure an exhaust gas which is produced in combustion of an air-fuel mixture at the stoichiometric ratio and which therefore has a low oxygen content. This oxygen sensor includes a planar solid electrolyte body 56 which is provided on its outer surface with a measuring electrode 58. The electrode 58 is connected via a lead 60 to an external device and exposed to the measurement gas through a porous protective layer 62 which covers the electrode 58. A reference electrode 64 with a lead 66 is disposed on the inner surface of the planar solid electrolyte body 56. A substantive portion of the lead 66, that is, the portion of the lead 66 which is exposed to an elevated temperature, is sandwiched by two electrical insulation layers 68 and 70. On the side of the planar solid electrolyte body 56 on which the reference electrode 64 is disposed, a U-shaped solid electrolyte body 72 and a planar solid electrolyte body 74 are superposed such that the U-shaped solid electrolyte body 72 is sandwiched by the two planar solid electrolyte bodies 56 and 74. The three solid electrolyte bodies 56, 72 and 74 cooperate to define a cavity 76 which is open at its one end to the ambient atmosphere. The reference electrode 64 is positioned so as to be exposed to a reference gas such as an ambient atmosphere introduced into the cavity 76.

In the above arrangement, the measuring electrode 58 exposed to the measurement gas through the protective layer 62, and the reference electrode 64 exposed to the reference gas, form an electrochemical cell which operates as an oxygen concentration cell in response to a difference in oxygen concentration between the measurement and reference gases.

On one side of the planar solid electrolyte body 74 remote from the U-shaped solid electrolyte body 72, there is provided a heating element 78 sandwiched by a pair of gastight ceramic layers 77, 79 which protect and electrically insulate the heating element 78. The heater heats a portion of the planar solid electrolyte body 56 adjacent to the electrodes 58, 64, to an elevated temperature so as to maintain a sufficient oxygen-ion conductivity of that portion of the solid electrolyte body 56.

In the oxygen sensor arranged as described above, the conductor disposed between the solid electrolyte bodies 56 and 72, that is, the lead 66 of the reference electrode 64 is sandwiched at its opposite surfaces by a pair of electrical insulation layers 68 and 70, and thereby electrically insulated with respect to the electrolyte bodies 56 and 72. In other words, the insulation layers 68, 70 prevent the lead 66 from directly contacting the solid electrolyte bodies 56, 72, and thereby eliminating an otherwise possible chance of erroneous measurement of an electromotive force between the lead 66, and the measuring electrode 58 which is more or less opposite to the lead 66. Thus, the output noises due to the lead 66 are effectively prevented.

Figure 7:
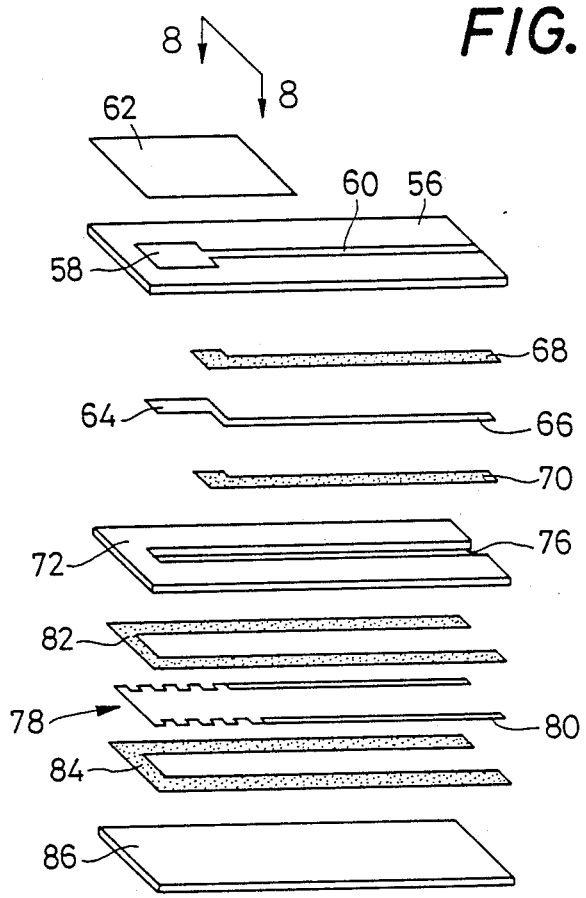
Figure 8:
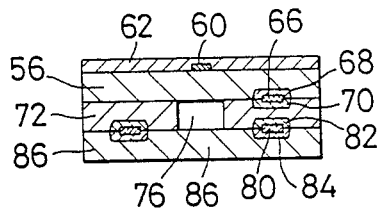

FIGS. 7 and 8 illustrate a further embodiment of the invention wherein the oxygen sensor is different from the sensor of FIGS. 5 and 6 in location and environments of the heater 78.

Stated in more detail, the heating element 78 and its leads 80 of this modified embodiment of the oxygen sensor are sandwiched at their substantive portions by a pair of electrical insulation layers 82, 84. The end portions of the leads 80 remote from the heating element 78 are exposed for electric connection to an external power source. These insulation layers 82, 84 laminated to sandwich the heating element 78 and the leads 80 are sandwiched by a solid electrolyte body 86, and the previously indicated U-shaped solid electrolyte body 72 having the cavity 76. The lead 66 of the reference electrode 64 is electrically insulated over its entire length by a pair of elongate insulation layers 68, 70.

If the heating element 78 were directly embedded between the solid electrolyte bodies 72 and 86, a portion of the electric current flowing in the heating element 78 and the leads 80 would leak through the solid electrolyte bodies 72, 86 when the heating element 78 is energized to heat the oxygen sensor, more precisely a portion of the planar solid electrolyte body 56 adjacent to the measuring and reference electrodes 58 and 64.

According to the present embodiment, however, not only the heating element 78 but also the leads 80 are electrically insulated relative to the solid electrolyte bodies 72 and 86 by the upper and lower electrical insulation layers 82 and 84, respectively. In other words, the electrolyte bodies 72, 86 are separated or spaced away from the heating element 78 and the leads 80 by the insulation layers 82, 84, and thus kept free from electrolysis due to energization of the heating element 78. Consequently, otherwise possible deterioration and cracking troubles with the solid electrolyte bodies 72, 86 due to the electrolysis will be effectively prevented. Further, the insulation layer 82 serves to hinder a leakage flow of current from reaching the reference electrode 64 through the solid electrolyte body 72, thus preventing an unfavourable influence of such leakage current upon the reference electrode 64.

While the present invention has been described in its preferred forms for illustrative purpose only, the electrochemical device of the invention is not limited to the illustrated details of constructions and arrangements; but it will be obvious to those skilled in the art that various changes, modifications and improvements may be made in the invention without departing from the spirit and scope of the invention.

Although the electrochemical devices according to the invention have been illustrated in the form of a sensor having an oxygen concentration cell, or a lean-burn sensor having an oxygen pumping cell as well as a sensing cell, various other forms of the electrochemical device may be constructed according to the invention. Further, the invention may be applied to an electrochemical pump, polarographic electrochemical cell, and the like.

What is claimed is:

1. An electrochemical device for determining or controlling the concentration of specific components of a fluid, comprising:

a plurality of solid electrolyte bodies;

at least one pair of electrodes in communcation with a gaseous fluid and in contacting engagement with exterior and interior surfaces of at least one of said plurality of solid electrolyte bodies;

at least one conductor disposed on said interior surface of said at least one solid electrolyte body, in electrical connection with each of the electrodes of said at least one pair of electrodes; and at least one electrical insulation layer located between at least one of said at least one conductor and said interior surface of said at least one solid electrolyte body upon which said at least one conductor is disposed, and covering a substantial portion of said at least one conductor, said at least one conductor being isolated from direct communication with any gaseous fluid, for effectively protecting said at least one solid electrolyte body against electrolysis.

2. The electrochemical device of claim 1, wherein at least a portion of said at least one conductor is surrounded by said electrical insulation layers, and said electrical insulation layers are sandwiched by two adjacent solid electrolyte bodies of said plurality of solid electrolyte bodies.

3. The electrochemcial device of claim 1, wherein said at least one conductor comprises a material including at least one element from the platinum group.

4. The electrochemical device of claim 1, wherein said at least one electrical insulation layer comprises a material consisting essentially of alumina or spinel.

5. The electrochemical device of claim 1, wherein said at least one conductor is a lead connected to one of said at least one pair of electrodes.

6. The electrochemical device of claim 1, wherein said plurality of solid electrolyte bodies comprise zirconia for detecting a concentration of oxygen in a sample gas.

7. An electrochemical device for determining the concentration of a component in a gaseous fluid, comprising:

a pumping cell having a laminar structure including a first planar solid electrolyte body, a pair of pumping electrodes in communication with a gaseous fluid and disposed in contact with opposite sides of said first planar solid electrolyte body, and a pair of first leads each being connected at a first end thereof to each of said pumping electrodes and at a second end thereof to an external power source;

a spacer member comprising a solid electrolyte material cooperating with said first planar solid electrolyte body to sandwich one of said pair of first leads therebetween so as to isolate said one of said pair of first leads from direct communication with any gaseous fluid;

a sensing cell having a laminar structure including a second planar solid electrolyte body, a pair of measuring electrodes in communication with a gaseous fluid and disposed in contact with said second planar solid electrolyte body, and a pair of second leads each being connected at a first end thereof to each of said measuring electrodes and at a second end thereof to an external measuring device, the laminar structures of said pumping cell and said sensing cell being disposed so as to sandwich said spacer member therebetween, at least one of said pair of second leads being sandwiched between said spacer member and said second planar solid electrolyte body, so as to be isolated from direct communication with any gaseous fluid;

a first and a second electrical insulation layer, said first electrical insulation layer being disposed between one side of said one of said pair of first leads and said first planar solid electrolyte body, and said second electrical insulation layer being disposed between a second side of said one of said pair of first leads and said spacer member; and a third electrical insulation layer disposed between one of said second leads which is sandwiched between said spacer member and said second planar solid electrolyte body, and said second planar solid electrolyte body;

whereby the solid electrolyte materials are effectively protected against electrolysis.

8. The electrochemical device of claim 7, wherein said spacer member includes a cavity into which and form which said component in the gaseous fluid is introduced and removed upon application of a voltage between said pumping electrodes.

9. The electrochemcial device of claim 8, wherein one of said pumping electrodes and one of said measuring electrodes are both exposed to said cavity formed in said spacer member.

10. The electrochemical device of claim 7 wherein said first and second leads comprise a material including elements of the platinum group.

11. The electrochemical device of claim 7, further comprising a heater having a laminar structure for heating said first and second planar solid electrolyte bodies which are adjacent to said pumping and measuring electrodes.

12. The electrochemical device of claim 11, wherein a fourth electrical insulation layer is disposed between said heater and said second planar solid electrolyte body.

13. The electrochemical device of claim 11, wherein said heater includes a heating element, leads connected to said heating elements, and a fourth electrical insulation layer disposed between said heating element or said leads, and said second planar solid electrolyte body.

14. The electrochemical device of claim 13, wherein said fourth electrical insulation layer comprises a material consisting essentially of alumunia or spinel.

15. The electrochemical device of claim 7, wherein said first, second and third electrical insulation layers comprise a material consisting essentially of alumina or spinel.

* * * * *